United States Patent [19]

Preusser et al.

[11] 4,410,400
[45] Oct. 18, 1983

[54] EXTRACTIVE DISTILLING WITH REWORKING OF RESIDUE

[75] Inventors: Gerhard Preusser, Essen; Martin Schulze, Neviges, both of Fed. Rep. of Germany

[73] Assignee: Krupp-Koppers GmbH, Essen, Fed. Rep. of Germany

[21] Appl. No.: 289,718

[22] Filed: Aug. 3, 1981

[30] Foreign Application Priority Data

Aug. 30, 1980 [DE] Fed. Rep. of Germany ....... 3032780

[51] Int. Cl.³ .......................... B01D 3/40; B01D 3/42
[52] U.S. Cl. .......................................... 203/3; 203/25; 203/27; 203/50; 203/74; 203/81; 203/98; 203/DIG. 19; 585/800
[58] Field of Search ........................................ 203/1–3, 203/21, 93, 98, DIG. 19, 25, 27, 50, 71, 73, 74, 81; 585/800; 202/158, 160, 162; 196/100, 132, 139, 140–142; 208/347, 350, 354, 355, 357, 358, 365, DIG. 1

[56] References Cited

U.S. PATENT DOCUMENTS 2,064,757  12/1936  Keith .................................. 208/355
4,162,198   7/1979  Stockburger et al. ..... 203/DIG. 19

*Primary Examiner*—Frank Sever
*Attorney, Agent, or Firm*—Michael J. Striker

[57] ABSTRACT

A method for working up residues of an extractive distilling process for obtaining pure hydrocarbons. The residue from an extractive distilling column is fed to the about middle part of a distilling column. The hydrocarbons are distilled and removed at the head of the distilling column and the solvent is removed at the bottom of the distilling column. A sidestream is removed from the distilling column at a position above the feed plate for the residue from the extractive distilling column via a so-called reflux evaporator plate having an elevated level of liquid. The sidestream is heated by indirect heat exchange with the solvent flowing from the distilling column. The heated-up sidestream is fed back into the distilling column at a level at or above the reflux evaporator plate. The concentration of the solvent at the reflux evaporator plate is controlled by the amount of reflux at the head of the distilling column.

The heating of the side stream reduces the heat requirement of the bottom boiler of the distilling column by about 35 percent.

14 Claims, 1 Drawing Figure

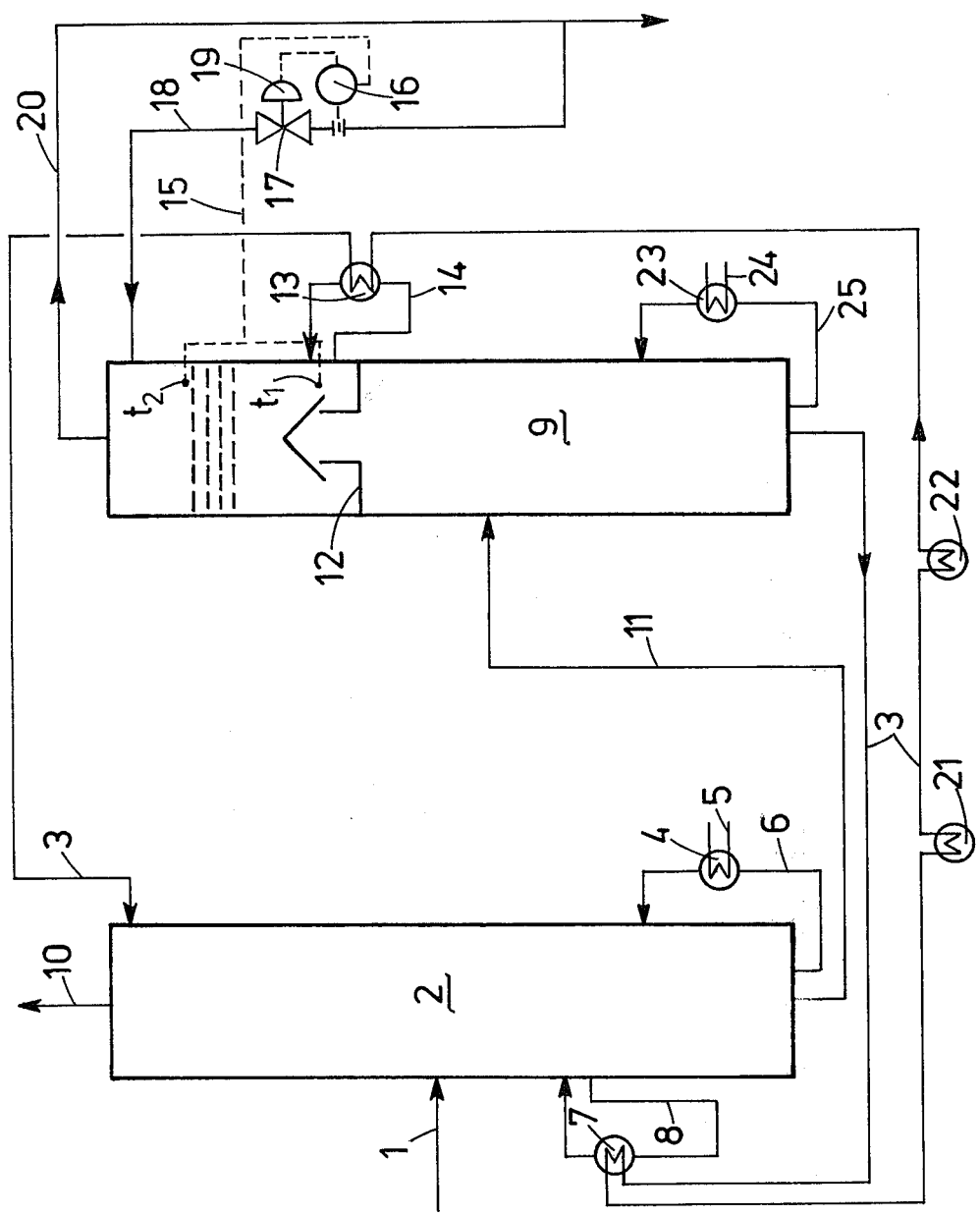

EXTRACTIVE DISTILLING WITH REWORKING OF RESIDUE

BACKGROUND OF THE INVENTION

1. Field of the Invention

The present invention relates to a method for reworking of the residue (bottom product) of extractive distilling processes for obtaining pure hydrocarbons and to an apparatus suitable for performing the method.

2. Brief Description of the Background of the Invention Including Prior Art

Extractive distilling is presently a widely employed method for separating mixtures of materials and in particular for separating mixtures of hydrocarbons, which based on the boiling points of their components cannot be separated or only to an unsatisfactory degree by distilling. As an example, the obtaining of pure aromatic hydrocarbons (benzene, toluene, xylene) from aromatic hydrocarbon containing starting materials, the separation of mono and diolefins as well as the separation of these olefins from non-aromatic hydrocarbons are mentioned. Such extractive distillation is taught for example in U.S. Pat. No. 3,679,579 (to G. Preusser et al.).

Numerous selective solvents have been proposed for performing such extractive distilling processes and N-substituted morpholine, in particular N-formyl-morpholine have proven to be advantageous solvents. The separating effect of the employed selective solvent is based on the effect that in its presence the partial pressures of the individual components of the mixture to be separated are changed such that the vapor pressure differences between those components, which are to be enriched in the extract and those components which are to be enriched in the raffinate is increased. Therefor, the latter can be distilled off as easier boiling fraction from the head of the extractive distilling column, while the less easily boiling components together with the major part of the solvent provide the residue of the extractive distilling column, the so-called bottom product or extract phase.

In order to separate the components to be obtained as an extract from the solvent, therefor the initially described reworking of the residues of the extractive distilling column is required in a following distilling column. Usually the distilling column is operated with a reflux of the components leaving at the head of the distilling column for achieving a good separation effect. The solvent leaving at the bottoms of the distilling column has an elevated temperature, which is for example in the case of the production of aromatic compounds depending on the operating conditions of the distilling column such as pressure and temperature in a region of from about 150° to 240° C. Before feeding back the solvents flowing out of the bottoms of the distilling column into the extractive distilling column it is required to cool the solvent down to from about 90° to 120° C.

In order to employ the heat content of the solvent flowing from the bottom of the distilling column it has been proposed to cool the solvent in indirect heat exchange with other product streams before feeding it back to the extractive distilling column. For example in the advertising flyer Koppers Bericht 333b of September 1969 there is indicated a process scheme for the production of pure o-xylene from reformate by extractive distilling, where the solvent flowing from the distilling column is used first in an indirect heat exchange to heating up the residue product of the distilling column and of the extractive distilling column. This mode of operation, however, does not provide for cooling of the solvent to the extent that its feeding back into the extractive distilling column is possible without further steps. Therefor, it has to be provided with a further cooling in an aircooler before being fed back to the extractive distilling column, whereby of course part of its heat content is lost without providing any use.

In fact, the economy of the solvent recovery from the residue product of the extractive distilling column and the therewith connected use of the heat content of the solvent separated from the hydrocarbons of the extract represent factors, which decisively influence the economy of the total process.

SUMMARY OF THE INVENTION

1. Purposes of the Invention

It is an object of the present invention to provide a method for reworking of the residue product of extractive distilling processes for obtaining pure hydrocarbons by way of improved use of the heat content of the solvent separated thereby and to provide a more economic distilling process.

It is another object of the present invention to provide an improved method of controlling the operation of the distilling column.

It is a further object of the present invention to provide an apparatus which minimizes the thermal energy required in the recovery of the products from extractive distilling.

These and other objects and advantages of the present invention will become evident from the description which follows.

2. Brief Description of the Invention

The present invention provides a method for working up residues of extractive distilling processes in order to obtain pure hydrocarbons. The residue from an extractive distilling column to be worked up is fed to about the middle part of a distilling column including plates and bottom boiler. The hydrocarbons are distilled off from the mixture in the distilling column and are removed at the head of the distilling column. The solvent is removed at the bottom of the distilling column. A sidestream is taken from the distilling column at a position above above the feed plate for the residue from the extractive distilling column via a so-called reflux evaporator plate with elevated level of liquid. The sidestream is heated by indirect heat exchange with the solvent flowing from the distilling column. The heated-up sidestream is fed back into the distilling column to a plate level at or above the reflux evaporator plate. The concentration of solvent at about the reflux evaporator plate is controlled by the amount of reflux at the head of the distilling column.

The solvent concentration at the level of the reflux evaporator plate can be maintained at a level of from about 10 to 70 weight percent and preferably is maintained at a level of 20 to 50 weight percent. There can be provided exchanging of heat between the solvent removed from the bottoms of the distilling column and other product streams. The solvent from the bottoms of the distilling column can be fed back to the solvent feed of the extractive distilling column. Preferably the solvent is cooled by exchanging heat with the sidestream to be heated up of the distilling column, to such a temperature at which the solvent is suitable for being fed back into the extractive distilling column.

There can be provided determining the concentration of the solvent at the reflux evaporation plate by analytical means such as gas chromatography, determination of density, determination of index of refraction, determination of temperature or determination of temperature differences. Preferably the temperature difference between the temperature at about the level of the reflux evaporator plate and the temperature at a level above the reflux evaporator plate are determined and the level above the reflux evaporator plate is preferred to be about from the fourth to sixth plate above the reflux evaporator plate. The amount of reflux can be increased with increasing temperature difference and the amount of reflux can be decreased with decreasing temperature difference.

A valve in a reflux return line can be actuated depending on the composition of the fluid at about the level of the reflux evaporator plate as determined by analytical means. The pressure in the distilling column is preferably from about 0.15 bar to atmospheric pressure. The starting mixture of the extractive distilling column can be a mixture of aliphatic and aromatic hydrocarbons.

There is also provided an apparatus for extractive distilling, where the residues of an extractive distilling column are reworked. An extractive distilling column is connected at about the middle part to a starting material feed line. A residue feed line is connected to the bottom of the extractive distilling column and at about the middle part to the residue of the feed line. A reflux evaporator plate is disposed in the distilling column above the connecting point of the residue feed line. A sidestream take-off line is connected to the distilling column at about the level of the reflux evaporator plate. A boiler is connected to the sidestream take-off line for providing thermal energy to the side stream. A sidestream feedback line connects the boiler to the distilling column at or above the reflux evaporator plate level. A sensor is provided for determining the composition of the fluid in the distilling column at about the relux evaporator plate level. A reflux return line is connected to the head of the column and a valve is disposed in the reflux return line and connected to the sensor for being actuated depending on the composition of the fluid at about the reflux evaporator plate level.

A second boiler can be connected to the bottom of the distilling column. A line for removal of the bottoms of the distilling column can be connected to the boiler for passing through the boiler and thereby providing heat to the sidestream. The line can continue and connect the boiler to the head of the extractive distilling column for transferring the bottoms of the distilling column to the head of the extractive distilling column. A heat exchanger can be disposed at the line for removal of the bottoms of the distilling column in order to transfer part of the thermal energy contained in the bottom product of the distilling column. The sensor can be a temperature sensing element. Preferably the sensor comprises two temperature sensing elements, one of which is disposed at about the level of the reflux evaporator plate and the second is disposed above the reflux evaporator plate for providing a signal about proportional to the temperature difference. The second temperature sensing element can be disposed at from about the fourth to the sixth plate above the reflux evaporator plate.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWING

In the accompanying drawing in which is shown one of the various possible embodiments of the present invention, The FIGURE is a view of a schematic diagram of the apparatus of the invention.

DESCRIPTION OF INVENTION AND PREFERRED EMBODIMENTS

In accordance with the present invention the residue product of an extractive distilling column to be worked up is fed into the middle part of a distilling column provided with plates and a bottom boiler. The products to be obtained are hydrocarbons, which are distilled off at the head of the distilling column. The solvent is withdrawn from the bottom of the distilling column and fed back to the solvent feed in of the extractive distilling column possibly after engaging in indirect heat exchange with other product streams. A sidestream is withdrawn from the distilling column via a so-called reflux evaporation plate with elevated liquid level disposed above the feed level plate for the residue product of the extractive distilling column. The sidestream is heated up by indirect heat exchange with the solvent flowing back to the extractive distilling column and is then fed to the distilling column at the reflux evaporator plate level or at a level above the reflux evaporator plate. The concentration of the solvent at the reflux evaporator plate level is controlled by the amount of reflux and is maintained at a value of from about 10 to 70 weight percent.

If operation is performed in accordance with the present invention, therefor a considerable part of the heat required for the operation of the distilling column, which conventionally had to be supplied at the bottom boiler of the distilling column by costly medium pressure steam, is made available by the indirect heat exchange with the solvent separated from the hydrocarbons of the extract. In view of the temperature situation in the distilling column, the operation temperature of which decreases from bottom to top, it does not make sense to perform this heat exchange in the lower part of the distilling column at a high temperature level. The present invention therefor provides that the side stream, which is to be heated up by indirect heat exchange with the solvent flowing back to the extractive distilling column, is only withdrawn from the upper part of the distilling column, that is above the feed plate level. For this purpose a so-called reflux evaporator is disposed at a position provided for it in the upper part of the distilling column and this reflux evaporator plate distinguishes from the other column plates by an elevated liquid level. This can be achieved without difficulty by applying a suitable plate construction such as for example a chimney plate (bubble plate). The reflux evaporating plate is usually about 3 to 5 plates above the feed plate. The sidestream withdrawn from the reflux evaporator plate is fed back to the distilling column after its reheating, which is performed by indirect heat exchange with the solvent in a correspondingly disposed boiler. The feeding back preferably is performed to the reflux evaporator plate itself or possibly from about 1 to 5 plates above the reflux evaporator plate. The solvent is cooled at the same time during passing the boiler and the operation conditions of the boiler are preferably controlled such that the cooling of the solvent is is performed up to such temperature, where it can without additional intermediate cooling be fed again to the extractive distilling column.

However, it has to be considered in the performance of the process of the present invention, that the reheating of the sidestream by way of indirect heat exchange with the solvent does not result in evaporating the total reflux fed to the distilling column, since part of the reflux has to run with the remainders of the solvent from the reflux evaporator plate to the lower part of the distilling column. Therefor, it is provided for the maintenance of optimal conditions that the concentration of the solvent at the level of the reflux evaporation plate is controlled by the amount of reflux returned to the distilling column and that preferably a value of from about 10 to 70 weight percent and better a value of from about 20 to 50 weight percent is maintained.

This means that the amount of reflux returned to the distilling column depends on the concentration of the solvent, which is determined at the level of the reflux evaporator plate. If the concentration of the solvent increases too much then the amount of reflux has to be increased accordingly, while reversely upon a decrease of the concentration of the solvent the amount of reflux can be decreased. Therefor it is required for the control of the invention method to determine the solvent concentration at the level of the reflux evaporator plate in a suitable way and to employ the resulting values as control values for the amount of reflux in the way and manner described above.

The following known measurement methods are in principle available for the determination of the concentration of the solvent:

(1) Determination by gaschromatography
(2) Measurement of Density
(3) Measurement of the index of refraction
(4) Measurement of temperature.

However, the measurements under (1) to (3) require expensive measurement equipment with sampling conduits from the reflux evaporator plate to the equipment and back. A temperature measurement according to (4) requires relatively little measuring equipment. However, since the distilling column usually is operated with pressure below atmospheric pressure, pressure variations possibly caused by various sources enter into the measurement and distort the measured value.

Although these measurement methods are in principle suitable for the purposes of the present invention, there was a need to eliminate the disadvantages of the above recited measurement methods. It has now surprisingly been found that a measurement of the temperature difference between the level of the reflux evaporator plate and another plate disposed higher as compared with the reflux evaporator plate results in a measurement value substantially independent from all interference factors affecting the distilling column and this difference value is suitable to serve as the control parameter for the amount of reflux. Preferably, the temperature is determined at the level of the reflux evaporator plate and at the level of a plate disposed about 4 to 6 plates higher than the reflux evaporator plate. The resulting temperature difference controls the amount of reflux such that with increasing $\Delta t$-value the amount of reflux is increased and that with decreasing $\Delta t$-value the amount of reflux is decreased. It has been found that upon employment of the measurement of the temperature difference according to the present invention, the amount of reflux fed to the distilling column can be controlled reliably and completely independent from possibly occuring pressure variations in the distilling column and at the same time the equipment requirements for performing the process according to the invention are relatively low.

Further details of the method of the present invention as well as its relation to the to the preperformed extractive distilling are to be illustrated in the following by way of the diagram shown in the FIGURE, which at the same time relates to a specific example.

Of course, the schematic diagram indicates only the indispensable parts of the equipment, while other side and auxiliary equipment such as pumps, valves etc. are not shown.

The starting material to be worked up and from which benzene is to be produced is fed via conduit 1 to the middle part of the extractive distilling column 2 provided with plates. The starting material in conduit 1 is provided at a temperature of 80° C. and has the following composition:

| Non-aromatics | 33 percent by weight |
|---|---|
| Benzene | 67 percent by weight |

In the present embodiment N-formyl-morpholine is employed as a selective solvent and the solvent is fed at a temperature of 103° C. via conduit 3 to the head of the extractive distilling column 2. A boiler 4 is provided at the column bottom for the heating of the extractive distilling column 2, which provides an indirect heating of the bottoms product with medium pressure steam fed via conduit 5. The residue product to be heated of the extractive distilling column 2 is withdrawn via conduit 6 and reaches after passing the boiler 4 again one of the plates above the bottom of the extractive distilling column 2. In addition, another boiler 7 is installed at the bottom part of the extractive distilling column 2, where the product flowing via conduit 8 is heated by indirect heat exchange with the solvent flowing through conduit 3 and coming from the distilling column 9.

The lower boiling components of the starting material leave the extractive distilling column 2 via the head and via conduit 10 and the residue product is withdrawn via conduit 11. The product in conduit 10, the raffinate, has the following composition:

| Non-aromatics | 97 percent by weight |
|---|---|
| Benzene | 2 percent by weight |
| Solvent | 1 percent by weight |

The residue product in conduit 11 (extract phase) comprises the benzene dissolved in the solvent. For further reworking and processing this residue product of the extractive distilling is fed via conduit 11 to the middle part of the distilling column 9 provided with plates. The third plate above the feed plate level is formed as a chimney plate with elevated liquid level in this column, which is operated at a pressure of from about 0.5 to 0.7 bar. The chimney plate serves as the so-called reflux evaporator plate 12 according to the present invention. A boiler 13 is disposed at the level of the chimney plate and is placed at the distilling column 9. The boiler 13 is heated by indirect heat exchange with the solvent flowing in conduit 3. A sidestream is withdrawn from the reflux evaporator plate 12 via conduit 14 and fed to the boiler 13 for reheating and thereafter the sidestream is returned to the reflux evaporator plate 12. The amount of heat provided in the boiler 13 for reheating the sidestream depends of course on the heat content of the solvent in this part of the conduit 3 as well as on the final temperature, to which the solvent is to be cooled while passing through the boiler 13.

The solvent is in the present case and preferred embodiment to be cooled to a temperature at which it can be fed again to the extractive distilling column 2. At the same time the concentration of the solvent at the level of the reflux evaporator plate 12 is to be maintained in a range from about 20 to 50 percent by weight. The control of the reflux amount required for this purpose is provided by the above described temperature difference determination. For this purpose at the reflux evaporator plate 12 the temperature measurement sensor $t_1$ is disposed and on the fourth plate above the temperature measurement sensor $t_2$ is provided. The first four plates disposed above the reflux evaporator plate 12 are shown in FIG. 1 by way of dashed lines. The temperature differences $\Delta t$ determined between $t_1$ and $t_2$ is transmitted via the dashed shown pulse line 15 to the flow rate controller 16, which via the setting of the valve 17 controls the amount of reflux flowing in line 18 and which is fed via this line 18 to the head of the distilling column 9. The setting drive 19 serves for actuation of the valve 17. In the present case the determined $\Delta t$-value has to be between 3° and 12° C. If this region is surpassed at the top, then by a corresponding actuation of the valve 17 the feed of reflux is increased via line 18 while in the opposite case, if the indicated range of $\Delta t$-values is not reached, then a decrease of the amount of reflux is achieved by automatically closing the valve 17 further. The line 18 serving for the feed of the reflux branches off from line 20 by way of which the head product of the distilling column 9 is withdrawn. The head product has the following composition:

| Benzene | more than 99.9 percent by weight |
| Non-aromatics | less than 0.1 percent by weight |
| Solvent | less than 1 ppm |

In addition there can be provided cooling provisions (reflux coolers) in the line 20 not shown in FIG. 1 for providing further cooling of the hydrocarbon stream passing through line 20. The bottom product of the distilling column 9 consisting essentially of solvent is in the meantime withdrawn from the distilling column 9 via conduit 3. In the flow diagram shown in FIG. 1 the solvent in line 3 passes initially the boiler 7, where it contributes in the way described above to to the heating of the extractive distilling column 2. In the further course of the conduit 3 there are provided in the present embodiment heat exchangers 21 and 22, wherein a part of the heat content of the solvent is employed in the indirect heat exchange for recovery of the solvent from the raffinate phase (21) coming from conduit 10 and for preheating of the starting material (22) introduced via conduit 1. Thereupon, the solvent in conduit 3 finally passes through the boiler 13, where its heat content is used in the way and manner described above in accordance with the present invention. While the solvent upon exiting from the distilling column 9 shows a temperature of about 200° C., its temperature after passing the circulation boiler 13 is only about 100° to 103° C. The solvent at this temperature can be fed again to the extractive distilling column 2 without further intermediate cooling.

However, it has to be pointed out that the boiler 7 as well as the heat exchangers 21 and 22 are optional features of the method of the present invention. If other starting materials and/or other solvents are employed and/or there are different temperature conditions in the distilling column, then these features can possibly fully or in part be eliminated, such that it is for example clearly possible, that the solvent flowing from the bottom of the distilling column 9 passes directly into the boiler 13. Since the boiler 13 however is insufficient for the heating of the distilling column 9, there is provided additionally at the column bottom in a conventional way the bottom boiler 23, which is heated via conduit 24 with medium pressure steam. The bottom product to be heated thereby is fed via conduit 25 to the bottom boiler 23 and thereupon again fed to the distilling column 9 at a point disposed above the withdrawal point. By applying the method of the present invention the bottom boiler 23 however is substantially released, such that its requirement of medium pressure steam can be reduced by about 35 percent.

It will be understood that each of the elements described above, or two or more together, may also find a useful application in other types of system configurations and distilling and extractive distilling procedures differing from the types described above.

While the invention has been illustrated and described as embodied in the context of an extractive distilling system for hydrocarbons, it is not intended to be limited to the details shown, since various modifications and structural changes may be made without departing from the spirit of the present invention.

Without further analysis, the foregoing will so fully reveal the gist of the present invention that others can, by applying current knowledge, readily adapt it for various applications without omitting features that, from the standpoint of prior art, faily constitute essential characteristics of the generic or specific aspects of this invention.

What is claimed as new and desired to be protected by Letters Patent is set forth in the appended claims:

1. Method for working up residues of extractive distilling process for obtaining pure hydrocarbons comprising feeding the residue to be worked up from an extractive distilling column to the about middle part of a distilling column including plates and bottom boiler;

distilling the hydrocarbons in the distilling column;

removing the hydrocarbons at the head of the distilling column;

removing the solvent at the bottom of the distilling column;

removing a sidestream from the distilling column at a position above the feed plate for the residue from the extractive distilling column via a so-called reflux evaporator plate with elevated level of liquid;

heating the sidestream by indirect heat exchange with the solvent flowing from the distilling column;

feeding back the heated-up side stream into the distilling column to a plate at or above the reflux evaporator plate; and controlling the concentration of solvent at the reflux evaporator plate by the amount of reflux at the head of the column.

2. The method for working up residues according to claim 1 wherein the solvent concentration at the reflux evaporator plate is maintained at a level of from about 10 to 70 weight percent.

3. The method for working up residues according to claim 2 wherein the solvent concentration at the reflux evaporator plate is maintained at a level of from about 20 to 50 weight percent.

4. The method for working up residues according to claim 1 further comprising feeding back the solvent from the bottoms of the distilling column to the solvent feed of the extracting distilling column.

5. The method for working up residues according to claim 4 further comprising cooling the solvent, exchanging heat with the sidestream of the distilling column to be heated up, to such a temperature at which it is suitable for being fed back into the extractive distilling column.

6. The method for working up residues according to claim 1 further comprising determining the concentration of the solvent at the reflux evaporation plate by analytical means.

7. The method for working up residues according to claim 6 wherein the analytical means includes gas chromatography.

8. The method for working up residues according to claim 6 wherein the analytical means includes determination of density.

9. The method for working up residues according to claim 6 wherein the analytical means includes determination of the index of refraction.

10. The method for working up residues according to claim 6 wherein the analytical means comprises determining the temperature difference between the temperature at about the level of the reflux evaporator plate and the temperature at a level above the reflux evaporator plate.

11. The method for working up residues according to claim 10 wherein the level above the reflux evaporator plate is from about the fourth to sixth plate above the reflux evaporator plate.

12. The method for working up residues according to claim 10 further comprising
increasing the amount of reflux with increasing temperature difference; and
decreasing the amount of reflux with decreasing temperature difference.

13. The method for working up residues according to claim 1 wherein the pressure in the distilling column is from about 0.15 bar to atmospheric pressure.

14. The method for working up residues according to claim 1 wherein the starting material of the extractive distilling column is a mixture of aliphatic and aromatic hydrocarbons.

* * * * *